US006368806B1

(12) United States Patent
Openshaw et al.

(10) Patent No.: US 6,368,806 B1
(45) Date of Patent: Apr. 9, 2002

(54) MARKER ASSISTED IDENTIFICATION OF A GENE ASSOCIATED WITH A PHENOTYPIC TRAIT

(75) Inventors: Steve Openshaw, Northfield, MN (US); Wesley B. Bruce, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/679,769

(22) Filed: Oct. 5, 2000

(51) Int. Cl.[7] .......................... C12Q 1/68; C07H 21/02; C07H 21/04; C12N 15/00
(52) U.S. Cl. ................. 435/6; 536/23.1; 536/24.3; 935/76; 935/77; 935/78
(58) Field of Search ............................. 435/6; 536/23.1, 536/24.3; 935/76, 77, 78

(56) References Cited

U.S. PATENT DOCUMENTS 5,492,547 A  *  2/1996  Johnson
5,756,023 A  *  5/1998  Hanafey et al.
5,908,978 A  *  6/1999  Amerson et al.
5,948,953 A  *  9/1999  Webb
6,040,138 A  *  3/2000  Lockhart et al.
6,219,964 B1 *  4/2001  Byrum et al.

OTHER PUBLICATIONS

Mansur et al., Theorectical Applied Genetics 86: 914–918 (Dec. 1993).*
Quarrie et al. J. of Experimental Botany 50 (337): 1299–1306 (Aug. 1999).*

* cited by examiner

*Primary Examiner*—Ethan C. Whisenant
(74) *Attorney, Agent, or Firm*—David B. Ran; Pioneer Hi-Bred International, Inc.

(57) ABSTRACT

The invention provides a method of associating a gene or an expression product with a complexly inherited phenotypic trait of interest in a plant. Plants are segregated by the presence or absence of a genetic marker. One or more of the segregated groups are expression profiled to determine the gene associated with the phenotypic trait of interest. The gene associated with the phenotypic trait of interest can be identified and/or isolated.

30 Claims, No Drawings

MARKER ASSISTED IDENTIFICATION OF A GENE ASSOCIATED WITH A PHENOTYPIC TRAIT

TECHNICAL FIELD

The present invention relates generally to the field of plant breeding. More specifically, it relates to gene identification in plants.

BACKGROUND OF THE INVENTION

The ability to predict the inheritance of certain traits is of tremendous value to agricultural, horticultural, and medical endeavors. For traits controlled by single genes, predicting inheritance patterns is often no more difficult than understanding simple Mendelian principles. However, traits controlled by more than one locus offer unique challenges. Statistical methods and experimental designs have been created in an attempt to predict the inheritance of numerous quantitatively inherited phenotypic traits.

However, attempts to compare gene expression between groups of organisms separated on the basis of phenotype of complexly inherited traits have still been frustrating because phenotypes are the result of environmental factors plus the effects of many genes. If a trait is complexly inherited, no individual in a segregating population is expected to carry all favorable or unfavorable alleles. Therefore, each group consists of expression products of both favorable and unfavorable alleles at loci affecting the trait.

What is needed in the art is a method to associate a gene or an expression product with a phenotypic trait of interest for use in such applications as predicting the inheritance of quantitatively inherited phenotypic traits and in separating groups of organisms on the basis of allelic variation rather than solely on phenotypic variation. The present invention provides these and other advantages.

SUMMARY OF THE INVENTION

Generally, it is the object of the present invention to provide methods of selection of a gene associated with a phenotypic trait. It is an object of the present invention to provide a method of associating a gene with a phenotypic trait of interest and methods of associating an expression product with a phenotypic trait of interest.

Therefore, in one aspect, the present invention relates to a method of associating a gene with a phenotypic trait of interest comprising (a) segregating members of a biological population by the presence or absence of one or more genetic markers statistically associated with a quantitatively inherited phenotypic trait; (b) expression profiling segregated members of (a); and, (c) determining from expression profiles of (b) the gene associated with said phenotypic trait.

In another aspect, the present invention relates to a method of associating an expression product with a phenotypic trait of interest comprising (a) segregating members of a population consisting of a biological population by the presence or absence of one or more genetic markers statistically associated with said phenotypic trait, wherein said phenotypic trait has a statistical association with more than one genetic locus; (b) expression profiling at least one segregated member of (a) possessing said genetic marker and at least one segregated member of (a) lacking said genetic marker; and, (c) determining from said expression profiles of (b) an expression product associated with said phenotypic trait.

In yet another aspect, the present invention relates to associating an expression product with a phenotypic trait of interest, comprising: (a) expression profiling a plurality of members of a biological population having one or more genetic markers statistically associated with a phenotypic trait of interest wherein said phenotypic trait exhibits statistical association with more than one genomic locus; (b) expression profiling a plurality of members from said population lacking said genetic marker; and, (c) determining from expression profiles of (a) and (b) an expression product associated with said phenotypic trait.

Definitions

The terms defined below are more fully defined by reference to the specification as a whole. Units, prefixes, and symbols may be denoted in their SI accepted form. Numeric ranges are inclusive of the numbers defining the range and include each integer within the defined range.

The phrase "biological population" includes reference to a group of individuals having the capacity to be genetically crossed, regardless of species. For example, a group of *Glycine soja* and *Glycine max* plants would be considered a "biological population" because they are capable of being crossed. Individuals, as used herein, will refer to whole organisms, organism organs, cells, and progeny of same. For example, a plant biological population would include reference to whole plants, plant organs, plant cells, seeds, suspension cultures, embryos, meristematic regions, callus tissue, leaves, roots, shoots, gametophytes, sporophytes, pollen, and microspores.

The phrase "expression profiling" includes reference to generating an expression profile. By "expression profile" is meant the quantitation of a plurality of DNA, RNA, or protein expression products from a cell, tissue or whole organism. Many RNA expression products of a cell or tissue can simultaneously be detected on a nucleic acid array, or by the technique of differential display or modification thereof, such as those described in WO 97/15690 by Rothberg et al. and U.S. Pat. No. 5,719,060.

By "genetic locus" is meant a location on a chromosome. By "genomic locus" is meant a location within the entire set of chromosomes of an organism.

As used herein, "linkage disequilibrium" refers to a statistical association between two loci or between a trait and a marker.

As used herein, "marker" includes reference to a locus on a chromosome that serves to identify a unique position on the chromosome. A genotype may be defined by use of one or a plurality of markers.

"Phenotypic traits" may be comprised of, but are not limited to, a combination of measurable traits reflected in, but not limited to, the following:

Barren plants: The percent of plants per plot that were barren (lack ears).

Brittle Stalks: This is a measure of the stalk breakage near the time of pollination, and is an indication of whether the stalk of a hybrid or inbred would snap or break near the time of flowering under severe winds.

Yield: Yield of the grain at harvest in bushels per acre adjusted to 15.5% moisture.

Disease resistance: Resistance to any plant pathogen or group of plant pathogens.

Drydown: The relative rate at which a hybrid will reach acceptable harvest moisture compared to other hybrids.

Dropped Ears: A measure of the number of dropped ears per plot and represents the percentage of plants that dropped ears prior to harvest.

Ear height: Ear height is a measure from the ground to the highest placed developed ear node attachment and is measured in inches.

General Ear Mold: This is based on overall rating for ear mold of mature ears without determining the specific mold organism, and may not be predictive for a specific ear mold.

European Corn Borer feeding resistance (Ostrinia nubilalis): Average inches of tunneling per plant in the stalk or post flowering degree of stalk breakage and other evidence of feeding by European Corn Borer.

European Corn Borer Dropped Ears (Ostrinia nubilalis): Dropped ears due to European Corn Borer. Percentage of plants that dropped ears under second generation corn borer infestation.

Early Growth: scored when two leaf collars are visible.

Early Stand Count: This is a measure of the stand establishment in the spring and represents the number of plants that emerge on per plot basis for the inbred or hybrid.

Growing Degree Units: Using the Barger Heat Unit Theory, that assumes that maize growth occurs in the temperature range 50° F.–86° F. and that temperatures outside this range slow down growth; the maximum daily heat unit accumulation is 36 and the minimum daily heat unit accumulation is 0. The seasonal accumulation of GDU is a major factor in determining maturity zones.

GDU to physical maturity: The number of growing degree units required for an inbred or hybrid line to have approximately 50 percent of plants at physiological maturity from time of planting. Growing degree units are calculated by the Barger method (described below).

GDU to shed: The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDU to silk: The number of growing degree units required for an inbred line or hybrid to have approximately 50 percent of the plants with silk emergence from time of planting. Growing degree units are calculated by the Barger Method as given in GDU SHD definition.

Grain Appearance: The general appearance of the shelled grain as it is harvested based on such factors as the color of harvested grain, any mold on the grain, and any cracked grain.

Harvest Moisture: The moisture is the actual percentage moisture of the grain at harvest.

Moisture Advantage: The moisture advantage of variety #1 over variety #2 as calculated by: Moisture of variety #2-Moisture of variety #1=Moisture Advantage of variety #1.

Grain Oil: The amount of the kernel that is oil, expressed as a percentage on a dry weight basis.

Plant Height: This is a measure of the height of the plant from the ground to the tip of the tassel in inches.

Pollen Score: Rating indicating the amount of pollen shed.

Pollen Weight: This is calculated by dry weight of tassels collected as shedding commences minus dry weight from similar tassels harvested after shedding is complete. Predicted Relative Maturity (PRM). This trait, predicted relative maturity, is based on the harvest moisture of the grain. The relative maturity rating is based on a known set of checks and utilizes standard linear regression analyses and is referred to as the Comparative Relative Maturity Rating System that is similar to the Minnesota Relative Maturity Rating System.

PRM Shed: Predicted relative maturity based on shed is based on the growing degree units (GDU) required to reach 50% pollen shed. Relative values are predicted values from the linear regression of observed GDU's on relative maturity of commercial checks.

Protein Rating: Comparison of relative amounts of protein in the grain compared to hybrids of similar maturity.

Root lodging: The percentage of plants that root lodge; plants that lean from the vertical axis at an approximately 30° angle or greater would be counted as root lodged.

Scatter Grain: lack of pollination or kernel abortion on the ear.

Seedling Vigor: The amount of vegetative growth after emergence at the seedling stage (approximately five leaves for maize).

Stay green: the measure of plant health near the time of black layer formation (physiological maturity).

Stand (%): the percent of stalks standing at harvest.

Stalk Count: the final stand or number of plants per plot.

Stalk Lodge: the percentage of plants that stalk lodged (stalk breakage) as measured by either natural lodging or pushing the stalks and determining the percentage of plants that break below the ear.

Tassel Blast: the degree of blasting (necrosis due to heat stress) of the tassel at the time of flowering.

Tassel Size: the relative size of the tassel.

Tassel Weight: this is the average weight of a tassel (grams) just prior to pollen shed.

Ear Texture: the relative hardness (smoothness of crown) of mature grain.

Number of tillers: a count of the number of tillers per plot that could possibly shed pollen.

ASI: the interval in GDU's between the GDU to shed and GDU to silk.

Grain composition amino acids: The average amount and type of amino acids present in the kernel based on 25 kernels.

Grain composition carbohydrate: The average amount and type of carbohydrate present in the kernel based on 25 kernels.

Ear length: The length of the ear from the base to the tip of the cob.

Kernel Row Count: The number of rows of kernels per ear.

Kernel per row: The average number of kernels per row based on at least 4 rows.

Ear diameter: The average diameter of the ear with intact kernels based on three measurements at different places on the ear.

Kernel row length: The average distance from the first kernel at the base of the ear to the last kernel at the tip of the ear.

KWT100: The average mass of kernel in grams for 100 kernels either as fresh tissue or dried to moisture level of 15.5%.

KWT300: The average mass of kernel in grams for 300 kernels either as fresh tissue or dried to moisture level of 15.5%.

The term "statistically associated" refers to the tendency of two events to occur together at a frequency greater than that attributable to chance, where the frequency attributable to chance is represented by a pre-determined level of significance. Statistical association can be determined by any one of a number of significance tests well known to those in the art, for example, ANOVA or t-tests. See, e.g. *Statistical Methods*, Snedecor, G. W. and Cochran, W. G., Iowa State University Press, Ames, Iowa (1985). Significance levels for α are preferably less than 0.01. For example, levels of significance for this invention could range between 0 and about 0.250, e.g. less than about 0.0001, 0.00050, 0.0010, 0.0050, 0.010, 0.025, 0.050, 0.100, or 0.250.

DETAILED DESCRIPTION OF THE INVENTION

The present invention provides, among other things, methods of associating a gene or an expression product with a phenotypic trait. Thus, the present invention provides utility in such exemplary applications as comparing gene expression between individuals or groups of individuals segregating for quantitatively inherited phenotypic traits. Advantageously, this method can be used in breeding programs to produce "clean" bulks, so that differences in expression profiles between the bulks reflect allelic variation at the markers. This method can also be used for the identification and isolation of genes associated with phenotypic traits.

Populations

The methods of the subject invention can be used with any biological population expressing a quantitative phenotypic trait. Those of skill in the art will recognize that the methods of this invention can be applied to a biological populations of any organism such as bacteria, yeast, insect, mammalian, or preferably plant populations. The present invention can be practiced over a broad range of plant types. For example, the invention can be used in species from the genera: Hordeum, Secale, Triticum, Sorghum (e.g., *S. bicolor*), Zea (e.g., *Z. mays*), Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, and Avena. More preferably, the plant species is selected from the group consisting of: maize, soybean, wheat, canola, sunflower, alfalfa, sorghum, and rice.

In preferred embodiments, the biological population used for the subject invention comprises at least 20 members. For example, a typical population includes between about 20 and 200 individuals but optionally may comprise at least about 20, 30, 40, 50, 60, 70, 80, 90, 100, 200, 300, 400, 500, 1,000, 2500, or 5,000 individuals.

Phenotypic Traits

The phenotypic trait selected for the current invention can be any quantitatively inherited phenotypic trait. In preferred embodiments, the phenotypic trait for a plant population is selected from the group consisting of: root lodging, stalk lodging, yield, insect resistance, and disease resistance. As those skilled in the art will readily recognize, the invention may be practiced using any phenotypic trait statistically associated with more than one genomic locus.

In some embodiments, the trait used in the subject invention can be a QTL ("QTL" see, Edwards, et al., (1987) in Genetics 116:113). QTL, or quantitative trait loci, are regions of the genome containing one more markers statistically associated with a trait measured on a quantitative scale. As is known by those in the art, this association can be determined using a simple ANOVA or t-test. See, e.g., Asins and Campbell, (1988) *Theor. Appl. Genet.* 76:623–226; *Statistical Methods*, Snedecor, G. W. and Cochran, W. G., Iowa State University Press, Ames, Iowa (1985); Haley and Knott, (1992) *Heredity* 69:315–324. For maximum likelihood methods see, e.g., Jansen and Stam (1994) *Genetics* 136:1447–1455, and Zeng (1994) *Genetics* 136:145–1468.

Genetic Markers

Members of the biological population are segregated on the basis of the presence or absence of at least one genetic marker statistically associated with the quantitatively inherited phenotypic trait of interest. The genetic marker includes such markers as: RFLPs, RAPDs, AFLPs, SSRs, and SNPs.

RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. Restriction fragments from homologous chromosomes are revealed. Differences in fragment size among alleles represent an RFLP (see, for example, Helentjaris et al., *Plant Mol. Bio.* 5:109–118 (1985), and U.S. Pat. No. 5,324,631).

In another embodiment, random amplified polymorphic DNA (RAPD) are used as genetic markers. The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland (1990), *Nucleic Acids Res.* 18:7213–7218; Hu and Quiros (1991) *Plant Cell Rep.* 10:505–511 ).

In yet another embodiment, amplified fragment length polymorphisms (AFLP) are used as a molecular marker. By AFLP technology is intended a process that is designed to generate large numbers of randomly distributed molecular markers (see, for example, European Patent Application No. 0534858 A1).

The phrase "simple sequence repeats" or "SSR" refers to di-, tri- or tetra-nucleotide tandem repeats within a genome. The repeat region may vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al (1996) *Theor. Appl. Genet.* 93:1071–1077; Bligh et al. (1995) *Euphytica* 86:83–85; Struss et al. (1998) *Theor. Appl. Genet.* 97:308–315; Wu et al. (1993) Mol. Gen. Genet. 241:225–235; U.S. Pat. No. 5,075,217). SSR are also known as satellites or microsatellites.

The phrase "single nucleotide polymorphism" or "SNP" refers to a single base pair difference variant sequence (see, for example, *Genome Analysis—A Laboratory Manual*, E. Green et al., Eds., Volume 4, Cold Spring Harbor Press, Cold Spring Harbor, N.Y., 1989; Ayres et al. (1997) *Theor. Appl. Genet.* 94:773–781; Landegren et al. (1998) *Genome Res.* 8:769–776; Wang et al. (1998) *Science* 280:1077–1082).

Many genetic markers suitable for use with the present invention are publicly available. Those skilled in the art can also readily prepare suitable markers. For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The segregated members of the biological population are expression profiled. The phrase "segregated members" includes reference to individuals or bulks.

Expression Profiling

Expression profiling can be performed using essentially any cell or collection of cells from the organism, or the whole organism. A variety of profiling methods are available, including hybridization of expressed or amplified nucleic acids to a nucleic acid array, hybridization of expressed polypeptides to a protein array, hybridization of peptides or nucleic acids to an antibody array, subtractive hybridization, differential display and, hybridization of either proteins or nucleic acids to an array of nucleic acids or proteins, respectively.

In one embodiment of the subject invention, the expression profile is an RNA profile. The expression products which are detected in the methods of the invention are RNAs, e.g., mRNAs expressed from genes within a cell of the plant or tissue profiled.

RNAs can be detected using any of several techniques available. For example, northern blot hybridization is widely used for RNA detection, and is generally taught in a variety of standard texts on molecular biology, including Berger and Kimmel, *Guide to Molecular Cloning Techniques, Methods in Enzymology*, volume 152, Academic Press, Inc., San Diego, Calif. ("Berger"); Sambrook et al., *Molecular Cloning—A Laboratory Manual* ($2^{nd}$ Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1998) ("Ausubel").

One of skill will appreciate that essentially any RNA can be converted into a double stranded DNA using a reverse transcriptase enzyme and a polymerase, see Ausubel, supra. Thus detection of mRNAs can be performed by converting, e.g., mRNAs into DNAs, which are subsequently detected in, e.g., a standard Southern blot technique.

These general methods can be used for expression profiling. For example, arrays of probes can be spotted onto a surface and expression products (or in vitro amplified nucleic acids corresponding to expression products) can be labeled and hybridized with the array. For convenience, it may be helpful to use several arrays simultaneously. It is expected that one of skill is familiar with nucleic acid hybridization. General methods of hybridization are found in Berger, Sambrook and Ausubel, supra, and further in Tijessen (1993) *Laboratory Techniques in Biochemistry and Molecular Biology—Hybridization with Nucleic Acid Probes*, e.g., part I chapter 2 "Overview of principals of hybridization and the strategy of nucleic acid probe assays," Elsevier, N.Y.

In one useful variation of these methods, solid phase arrays are adapted for the rapid and specific detection of multiple polymorphic nucleotides. Typically, a nucleic acid probe is chemically linked to a solid support and a target nucleic acid (e.g., an RNA or corresponding amplified DNA) is hybridized to the probe. Either the probe, or the target, or both, can be labeled, typically with a fluorophore. Where the target is labeled, hybridization is detected by detecting bound fluorescence. Where the probe is labeled, hybridization is typically detected by quenching of the label by the bound nucleic acid. Where both the probe and the target are labeled, detection of hybridization is typically performed by monitoring a signal shift such as a change of color, fluorescent quenching, or the like, resulting from proximity of the two bound labels. Where the probe is a mass label, the mass of the label can be detected quantitatively by mass spectrometer.

In one embodiment of this concept, an array of probes are synthesized on a solid support. Using chip masking technologies and photoreceptive chemistry, it is possible to generate ordered arrays of nucleic acid probes with large numbers of probes. These arrays, which are known, e.g., as "DNA chips," or as very large scale immobilized polymer arrays can include millions of defined probe regions on a substrate having an area of about 1 $cm^2$ to several $cm^2$. In addition to photomasking technologies, arrays of chemicals, nucleic acids, proteins, or the like can also be printed on a solid substrate using panting technologies.

The construction and use of solid phase nucleic acids arrays to detect target nucleic acids is well described in the literature. See, Fodor, et al. *Science* 251:767 (1991); Sheldon, et al. *Clin. Chem.* 39(4):718 (1993); Kozal, et al. *Nature Medicine* 2(7):753 (1996) and Hubbell, U.S. Pat. No. 5,571,639. In brief, a combinatorial strategy allows for the synthesis of arrays containing a large number of probes using a minimal number of synthetic steps. For instance, it is possible to synthesize and attach all possible DNA 8-mer oligonucleotides ($4^8$, or 65,536 possible combinations) using only 32 chemical synthetic steps. In general, these procedures provide a method of producing $4^n$ different oligonucleotide probes on an array using only $4^n$ synthetic steps.

In addition to being able to design, build and use probe arrays using available techniques, one of skill is also able to order custom-made arrays and array-reading devices from manufacturers specializing in array manufacture. For example, Affymetrix Corp. (Santa Clara, Calif.) manufactures nucleic acid arrays.

It will be appreciated that probe design is influenced by the intended application. For example, where several allele-specific probe-target interactions are to be detected in a single assay, e.g. on a single nucleic acid chip, it is desirable to have similar melting temperatures for all the probes. Accordingly, the length of the probes are adjusted so that the melting temperatures for all the probes on the array are closely similar (it will be appreciated that different lengths for different probes may be needed to achieve a particular $T_m$ where different probes have different GC contents). Although melting temperature is a primary consideration in probe design, other factors are also optionally used to further adjust probe construction, such as elimination of self-complementarity in the probe (which can inhibit hybridization of a target nucleotide). Techniques for designing and using sets of probes for screening many nucleic acids, such as expression products, simultaneously, and for monitoring expression on nucleic acid arrays are described in EP 0799 897 A1. Those of skill in the art are aware that one can moderate temperature effects by modifying the chemical composition of the nucleic acids on the array or of the hybridization solution.

One way to compare expression products between two cell populations is to identify mRNA species which are differentially expressed between the cell populations (i.e., present at different abundance levels between the cell populations). In addition to the array techniques noted above, another method is to use subtractive hybridization (Lee et al. (1991) *Proc. Natl. Acad. Sci. (U.S.A)* 88:2825) or differential display employing arbitrary primer polymerase chain reaction (PCR) (Liang and Pardee (1992) *Science* 257:967). Each of these methods has been used by various investigators to identify differentially expressed mRNA species. See, Salesiotis et al. (1995) *Cancer Lett.* 91:47; Jiang et al. (1995) *Oncogene* 10:1855; Blok et al. (1995) *Prostate* 26:213; Shinoura et al. (1995) *Cancer Lett.* 89:215; Murphy et al. (1993) *Cell Growth Differ.* 4:715; Austruy et al. (1993) *Cancer Res.* 53:2888; Zhang et al. (1993) *Mol. Cell. Endocrinol.* 108:108; Douglass et al. (1995) *J. Neurosci.* 15:2471; Aiello et al. (1994) *Proc. Natl. Acad. Sci. (U.S.A)* 91:6231; Ace et al. (1994) *Endocrinology* 134:1305.

For the technique of differential display, Liang and Pardee (1992), supra, provide theoretical calculations for the selection of 5' and 3' arbitrary primers. Correlation of observed results to the theory is also provided. In practice, 5' primers of less than about 9 nucleotides may not provide adequate specificity (slightly shorter primers of about 8 to 10 nucleotides have been used in PCR methods for analysis of DNA polymorphisms). See also, Williams et al. (1991) *Nucleic Acids Research* 18, 6531). The primer(s) optionally comprise 5'-terminal sequences which serve to anchor other PCR primers (distal primers) and/or which comprise a restriction site or half-site or other ligatable end. Where a restriction site or amplification template for a second primer is incorporated, the primers are optionally longer than those described above by the length of the restriction site, or amplification template site. Standard restriction enzyme sites include 4 base sites, 5 base sites, 6 base sites, 7 base sites, and 8 base sites. An amplification template site for a second primer can be of essentially any length, for example, the site can be about 15–25 nucleotides in length.

The amplified products are optionally labeled and are typically resolved by electrophoresis on a polyacrylamide gel; the location(s) where label is present are excised and the labeled product species is/are recovered from the gel portion, typically by elution. The resultant recovered product species can be subcloned into a replicable vector with or without attachment of linkers, amplified further, and/or detected, or even sequenced directly. Sequencing methods are described in Berger, Sambrook and Ausubel, supra. Direct sequencing of PCR generated amplicons by selectively incorporating boronated nuclease resistant nucleotides into the amplicons during PCR and digestion of the amplicons with a nuclease to produce sized template fragments has also been proposed (Porter et al. (1997) *Nucleic Acids Research* 25(8):1611–1617).

It is expected that one of skill can use differential display for expression profiling. In addition, companies such as CuraGen Corp. (New Haven, Conn.) provide robust expression profiling based upon modified differential display techniques. See, e.g., WO 97/15690 by Rothberg et al.

Expression profiling methods are used to determine a gene or an expression product statistically associated with the phenotypic trait of interest. For genes or expression products associated with the marker, one group will have alleles favorable for the trait while the other group will have unfavorable alleles. By comparing differences in expression between the groups segregated on the basis of the presence or absence of at least one genetic marker, genes or expression products associated with the trait can be identified.

In a preferred embodiment of the present invention, members possessing the gene or expression product exhibit at least a 2-fold variation relative to members lacking said genetic marker. For example, the gene or expression product could exhibit variation in expression between members possessing the marker and relatives lacking the marker of at least 2-fold, 3-fold, 4-fold, 5-fold, 6-fold, 7-fold, 8-fold, 9-fold, or 10-fold All publications, patents, and patent applications cited herein are hereby incorporated by reference.

What is claimed is:

1. A method of associating a gene with a phenotypic trait of interest, comprising:
   (a) segregating members of a biological population by the presence or absence of at least one genetic marker in linkage disequilibrium with said phenotypic trait, wherein said phenotypic trait is statistically associated with more than one genetic locus;
   (b) expression profiling segregated members of (a); and,
   (c) determining from expression profiles of (b) said gene associated with said phenotypic trait.

2. The method of claim 1, wherein said population is a plant population.

3. The method of claim 1, wherein said genetic marker is selected from the list consisting of: RFLPs, RAPDs, AFLPs, SSRs, and SNPs.

4. The method of claim 2, wherein said phenotypic trait is selected from the group consisting of: root lodging, stalk lodging, yield, insect resistance, and disease resistance.

5. The method of claim 1, wherein said population comprises at least 20 members.

6. The method of claim 1, wherein said trait is a QTL.

7. The method of claim 1, wherein the expression profile is an RNA profile.

8. The method of claim 1, wherein said gene exhibits at least a 2-fold variation in expression between members possessing said genetic marker relative to members lacking said genetic marker.

9. The method of claim 2, wherein said members are selected from the group consisting of: maize, canola, wheat, soybeans, sorghum, alfalfa, rice, and sunflower.

10. The method of claim 1, wherein said genetic marker is a gene associated with said phenotypic trait and not said gene of step (c).

11. A method of associating an expression product with a phenotypic trait of interest, comprising:
    (a) segregating members of a population consisting of a biological population by the presence or absence of at least one genetic marker statistically associated with said phenotypic trait, wherein said phenotypic trait has a statistical association with more than one genetic locus;
    (b) expression profiling at least one segregated member of (a) possessing said genetic marker and at least one segregated member of (a) lacking said genetic marker; and,
    (c) determining from said expression profiles of (b) an expression product associated with said phenotypic trait.

12. The method of claim 11, wherein said population is a plant population.

13. The method of claim 11, wherein said genetic marker is selected from the list consisting of: RFLPs, RAPDs, AFLPs, SSRs, and SNPs.

14. The method of claim 12, wherein said phenotypic trait is selected from the group consisting of: root lodging, stalk lodging, yield, insect resistance, and disease resistance.

15. The method of claim 11, wherein said population comprises at least 20 members.

16. The method of claim 11, wherein said trait is a QTL.

17. The method of claim 11, wherein the expression profile is an RNA profile.

18. The method of claim 11, wherein said gene exhibits at least a 2-fold variation in expression between members possessing said genetic marker relative to members lacking said genetic marker.

19. The method of claim 12, wherein said members are selected from the group consisting of: maize, canola, wheat, soybeans, sorghum, alfalfa, rice, and sunflower.

20. The method of claim 11, wherein said genetic marker is an expression product associated with said phenotypic trait and not said expression product of step (c).

21. A method of associating an expression product with a phenotypic trait of interest, comprising:
    (a) expression profiling a plurality of members of a biological population having at least one genetic marker in linkage disequilibrium with a phenotypic trait of interest wherein said phenotypic trait exhibits genetic linkage to more than one genomic locus;

(b) expression profiling a plurality of members from said population lacking said genetic marker; and, (c) determining from expression profiles of (a) and (b) an expression product associated with said phenotypic trait.

22. The method of claim 21, wherein said population is a plant population.

23. The method of claim 21, wherein said genetic marker is selected from the list consisting of: RFLPs, RAPDs, AFLPs, SSRs, and SNPs.

24. The method of claim 22, wherein said phenotypic trait is selected from the group consisting of: root lodging, stalk lodging, yield, insect resistance, and disease resistance.

25. The method of claim 21, wherein said population comprises at least 20 members.

26. The method of claim 21, wherein said trait is a QTL.

27. The method of claim 21, wherein the expression profile is an RNA profile.

28. The method of claim 21, wherein said gene exhibits at least a 2-fold variation in expression between members possessing said genetic marker relative to members lacking said genetic marker.

29. The method of claim 22, wherein said members are selected from the group consisting of: maize, canola, wheat, soybeans, sorghum, alfalfa, rice, and sunflower.

30. The method of claim 21, wherein said genetic marker is an expression product associated with said phenotypic trait and not said expression product of step (c).

* * * * *